(12) United States Patent
Nakagawara et al.

(10) Patent No.: US 7,429,451 B2
(45) Date of Patent: Sep. 30, 2008

(54) NUCLEIC ACIDS ISOLATED FROM STAGE 4 NEUROBLASTOMA

(75) Inventors: Akira Nakagawara, Chiba (JP); Miki Ohira, Chiba (JP)

(73) Assignees: Hisamitsu Pharmaceutical Co., Inc., Tosu-shi (JP); Chiba-Prefecture, Chiba-shi (JP)

( * ) Notice: Subject to any disclaimer, the term of this patent is extended or adjusted under 35 U.S.C. 154(b) by 353 days.

(21) Appl. No.: 10/533,158

(22) PCT Filed: Oct. 30, 2003

(86) PCT No.: PCT/JP03/13932

§ 371 (c)(1),
(2), (4) Date: Aug. 30, 2005

(87) PCT Pub. No.: WO2004/039975

PCT Pub. Date: May 13, 2004

(65) Prior Publication Data

US 2007/0281296 A1 Dec. 6, 2007

(30) Foreign Application Priority Data

Oct. 30, 2002 (JP) ............................. 2002-316586

(51) Int. Cl.
*C12Q 1/68* (2006.01)
*C07H 21/02* (2006.01)

(52) U.S. Cl. .......................................... 435/6; 536/23.1

(58) Field of Classification Search ....................... None
See application file for complete search history.

(56) References Cited

U.S. PATENT DOCUMENTS

2003/0207286 A1 11/2003 Nakagawara et al.
2004/0181048 A1* 9/2004 Wang ........................ 536/24.3

FOREIGN PATENT DOCUMENTS

WO  WO 01/66719 A1  9/2001
WO  WO 01/66733 A1  9/2001

OTHER PUBLICATIONS

Tockman et al (Cancer Res., 1992, 52:2711s-2718s).*
Rehman et al (Nucleic Acids Research, Jan. 1999, 27(2):649-655).*
Kawamoto et al., Association Between Favorable Neuroblastoma and High Expression of the Novel Metalloproteinase Gene, *nbla3145/XCE*, Cloned by Differential Screening of the Full-Length-Enriched Oligo-Capping Neuroblastoma cDNA Libraries, Medicinal and Pediatric Oncology, 35:628-631 (2000).

Islam et al., High Expression of *Survivin*, mapped to 17q25, is significantly associated with poor prognostic factors and promotes cell survival in human neuroblastoma, Oncogene, 19:617-623 (Feb. 3, 2000).
Aoyama et al., High Expression of Human RIM Gene in neuroblastomas with favorable biologies, 31st Annual Meeting of the Society for Neuroscience in San Diego, CA Nov. 10-15, 2001, Society for Neuroscience Abstracts, 27:715 (2001).
Tang et al., Implications fo EPHB6, EFB2, and EFNB3 expressions in human neuroblastoma, Proceedings of the National Academy of Sciences of the United States of America, 97:10936-10941 (Sep. 26, 2000).
*Homo sapiens* BAC Clone RP11-650J17 from 4, complete sequence, Database EMBL [OnLine], EBI Accession No. EM_PRO:AC093879 (Sep. 11, 2001).
Akira Nakagawara, "The gene which controls biology of neuroblastoma", Japanese Journal of Pediatric Medicine, vol. 30, No. 2, 1998-2, pp. 143-148.
"Sounding board, regression of neuroblastoma IV-S: a genetic hypothesis", The New England Journal of Medicine, May 29, 1980.
Akira Nakagawara, "Topical topic, the NGF story and neuroblastoma", Medical and Pediatric Oncology, 31:113-115 (1998), 1998 Wiley-Liss, Inc.
"Expression and prognosis of TRK family receptor in neuroblastoma", Shoni Geka (Pediatric Surgery), vol. 29, No. 3, 1997, pp. 425-432.
"Genetic events in neuroblastoma", Molecular Medicine, vol. 36, No. 4, 1999, pp. 366-372.
Eggert, A. et al., "High-level expression of angiogenic factors is associated with advanced tumor stage in human neuroblastomas", Clinical Cancer Research, vol. 6, 1900-1908, May 2000.
Gallego, S. et al., "Differential polymerase chain reaction with serial dilutions for quantification of MYCN gene amplification in neuroblastoma", Anticancer Research, vol. 18, pp. 1211-1216 (1998).
S. Yamane, "Gene Expression of tumor rejection antigens recognized by cytolytic T lymphocytes in neuroblastoma-related tumors", Journal of Kyoto Prefectual University of Medicine, vol. 108, No. 3, pp. 381-388 (1999).
The Sanger Centre, et al., "Toward a complete human genome sequence", Genome Research, vol. 8, pp. 1097-1108 (1998).

* cited by examiner

*Primary Examiner*—Misook Yu
*Assistant Examiner*—Sean Aeder
(74) *Attorney, Agent, or Firm*—Fitch, Even, Tabin & Flannery

(57) ABSTRACT

Diagnostic agent or kit for the prognosis of neuroblastoma is used to diagnose the prognosis of neuroblastoma (particularly, classifying its progress and determining stage 4s neuroblastoma), which agent or kit comprising a nucleic acid probe, nucleic acid primers, or a nucleic acid microarray utilizing a nucleic acid comprising one sequence selected from the group consisting of nucleic acids set forth in SEQ ID NO:1 to SEQ ID NO:174, a fragment thereof, or a combination of either or both.

9 Claims, No Drawings

NUCLEIC ACIDS ISOLATED FROM STAGE 4 NEUROBLASTOMA

This Application is the U.S. National Phase of International Application No. PCT/JP03/13932 filed Oct. 30, 2003, and claims foreign priority from Japanese Application No. 2002-316586, filed Oct. 30, 2002, the complete disclosures of which, including any and all sequence listings, are incorporated herein by reference.

TECHNICAL FIELD

Sequence Listing

The instant application contains a "lengthy" Sequence Listing which has been submitted via CD-R in lieu of a printed paper copy, and is hereby incorporated by reference in its entirety. Said CD-R, recorded on Apr. 26, 2007, are labeled CRF, "Copy 1" and "Copy 2", respectively, and each contains only one identical 672 KB file (73884325.APP).

This invention relates to nucleic acids derived from genes expressed in human neuroblastoma. More particularly, the invention relates to nucleic acids derived from genes expressed in human stage 4s neuroblastoma. Further, this invention relates to diagnostic agents and diagnostic kits for stage 4s neuroblastoma comprising nucleic acid probes, nucleic acid primers or nucleic acid microarrays utilizing those nucleic acids, their fragments, or the combinations of the foregoing, as well as to the elucidation of the mechanism of the programmed cell death of cancer cells based on the nucleic acid sequence data from the abovementioned genes.

BACKGROUND ART (Tumorgenesis and Genes)

Individual tumors exhibit distinct characteristic natures, and their biological properties are not necessarily identical even though the basic principle of oncogenesis is the same. Rapid advances in the understanding of cancer from a molecular biological and molecular genetic perspective in recent years have opened the way to an explanation of oncogenesis and the so-called tumor cell biology on the genetic level.

(Neuroblastoma)

Neuroblastoma is a pediatric cancer occurring in sympathetic gangliocytes and adrenal medullary cells which originate from cells of the peripheral sympathetic nervous system. Of these sympathetic neurons, neural crest cells in the initial stage of development migrate to the abdomen, differentiating and maturing at sites where sympathetic ganglia are formed. Some of these cells migrate further to the adrenal bodies, penetrating through the adrenal cortex which is already in the process of formation, and reaching the medulla and forming medullary substance there. The neural crest cells also serve as a source of other peripheral nerve cells, differentiating into dorsal root ganglia (sensory nerves), skin pigment cells, thyroid C cells, some pulmonary cells, intestinal gangliocytes, and the like.

(Prognosis for Neuroblastoma)

Neuroblastoma is characterized by a varied clinical profile (Nakagawara, Shinkeigashu no Hassei to Sono Bunshi Kiko [Neuroblastoma Development and Molecular Mechanism], Shoni Naika [Japanese Journal of Pediatric Medicine], Vol. 30, p. 143, 1998). For example, neuroblastoma occurring at less than one year of age has very favorable prognosis, with the majority undergoing differentiation and cell death, and results in spontaneous regression (which may be referred to as "favorable prognosis type"). Currently, most neuroblastomas discovered by a positive result in the commonly performed mass screening of 6-month-old infant urine are of the type which tend to undergo this spontaneous regression. On the other hand, neuroblastoma occurring at age 1 or higher is highly malignant and leads to death of the infant in the majority of cases despite therapy (which may be referred to as "unfavorable prognosis type"). It is also hypothesized that a somatic mutation occurs in highly malignant neuroblastomas in infants older than one year of age, which are of monoclonal nature, whereas in naturally regressing neuroblastomas, the genetic mutation remains at only a germ line mutation. See Knudson A G, et al.: Regression of neuroblastoma IV-S: A genetic hypothesis, N. Engl. J. Med., Vol. 302, p. 1254, 1980. In addition, there are known neuroblastomas of the intermediate type that are clinically positioned between those two types.

When the neuroblastomas are classified according to the progress of tumorization, they are as follows:

Stage 1: the tumor occurs primarily in adrenal gland or sympathetic ganglia and is confined.

Stage 2: the tumor is characterized by being confined to the site of origin and regional metastasis only to lymph nodes, which does not extends beyond the median line.

Stage 3: the tumor extends beyond the median line to invade into the opposite side or to metastasize into lymph nodes.

Stage 4: the tumor causes distant metastasis to bone, bone marrow or the orbital region.

Stage 4s: the tumor occurs at less than one year of age and causes distant metastasis to bone marrow, skin or liver.

The neuroblastomas of the favorable prognosis type are tumors at stages 1, 2, and 4s, while the neuroblastomas of the unfavorable and intermediate types are tumors at stages 3 and 4. The tumor at stage 4s is peculiar and normally occurs in an infant at several months after birth. Although the tumor grows and metastasizes quickly, it suddenly stops growing and then disappears spontaneously. Thus, the tumors that regress spontaneously and the tumors that grow malignantly are clearly distinct, with respect to the age of onset, the site of metastasis, and the progress.

(Genes which Allow the Prediction of Prognosis for Neuroblastoma)

With recent advances in molecular biology research, it has become clear that expression of the high affinity nerve growth factor (NGF) receptor TrkA is closely connected with control of differentiation and cell death (see Nakagawara A., The NGF story and neuroblastoma, Med. Pediatr. Oncol., vol. 31, p. 113, 1998). Trk is a membrane-spanning receptor, existing as the three major types, Trk-A, -B and -C.

These Trk family receptors play an important role in specific nerve cell differentiation and survival in the central nervous and peripheral nervous systems (see Nakagawara, et al., Shinkeigasaiboushu ni Okeru Neurotrophin Juyoutai no Hatsugen to Yogo [Expression of Neurotrophin Receptors and Prognosis in Neuroblastoma], Shoni Geka (Japanese Journal of Pediatric Surgery), Vol. 29, pp. 425-432, 1997). The survival and differentiation of tumor cells is controlled by signals from Trk tyrosine kinase and Ret tyrosine kinase. In particular, the role of TrkA receptor is most significant, with TrkA expression being notably high in neuroblastomas of the favorable prognosis type, and its signals exerting a powerful control over the survival and differentiation of tumor cells, and cell death (apoptosis). In neuroblastomas of the unfavorable prognosis type, on the other hand, TrkA expression is significantly suppressed, while tumor development is aided by a mechanism in which survival is promoted by signals from TrkB and Ret, instead.

It has become clear that amplification of the neural oncogene N-myc is associated with the prognosis of neuroblastoma (see Nakagawara, Nou-shinkeishuyo no Tadankai Hatsugan [Multistage Oncogenesis of Cerebral and Neural Tumors], Molecular Medicine, Vol. 364, p. 366, 1999). This gene, first cloned in neuroblastoma, is ordinarily only present in a single copy per haploid set in normal cells and neuroblastomas of the favorable prognosis type, whereas it has been found to be amplified several dozen times in neuroblastomas of the unfavorable prognosis type.

In addition to the genes described above, CD44, PTN, caspase and others are known as the gene whose expression is high in neuroblastomas of the favorable prognosis type, whereas SVV (survivin), MK (midkine) and others are known as the gene whose expression is high in neuroblastomas of the unfavorable prognosis type.

Furthermore, the present inventors found that a group of novel genes was highly expressed in neuroblastomas of the favorable prognosis type (International Publication PCT/JP01631 pamphlet). By contrast, the present inventors found that a different group of novel genes was highly expressed in neuroblastomas of the unfavorable prognosis type (International Publication PCT/JP01629 pamphlet).

Up till the present time, however, there has hardly been any information concerning the genes which are expressed in stage 4s neuroblastoma, particularly with specificity. Further, since stage 4s neuroblastoma regresses spontaneously, there is an urgent need to identify the causative genes.

DISCLOSURE OF THE INVENTION

This invention has been accomplished in light of the problems inherent in the above-described prior art, and its object is to identify the nucleic acid sequences of genes which are generally related to the favorable or unfavorable prognosis of neuroblastoma, and to allow for providing such genetic information and for diagnosis for the prognosis of neuroblastoma (whether favorable or unfavorable). This invention specifically aims at diagnosing the prognosis of neuroblastoma, classifying the progress of the neuroblastoma, and enabling the determination of stage 4s neuroblastoma.

As a result of conducting diligent research, the present inventors have examined the prognoses of neuroblastomas and have succeeded in constructing cDNA libraries from the respective clinical tissues of the favorable and unfavorable prognosis types. Approximately 2,400 clones were respectively cloned from these two types of cDNA libraries and were classified according to the prognoses of neuroblastomas (whether favorable or unfavorable). Profiling of the genes in the respective subsets was then carried out.

Thus, the present inventors found that a group of genes showed differential expression levels among the above-mentioned subsets and showed enhanced expression levels only in the clinical tissues of the favorable prognosis type. Moreover, the present inventors found that a group of genes showed enhanced expression levels only in the clinical tissues of the unfavorable prognosis type. Based on such finding, the present inventors made it possible to provide nucleic acid sequence data which would allow the detection and cloning of genes whose expression levels are at least enhanced either only in the clinical tissues of the favorable prognosis type or only in the clinical tissues of the unfavorable prognosis type.

Furthermore, the present inventors have succeeded in constructing cDNA libraries similarly from the clinical tissues of stage 4s neuroblastoma. Approximately 2,700 clones were cloned from this library. The subset of this library and the subsets of the libraries from the clinical tissues of the favorable and unfavorable prognosis types were analyzed and the profiling of approximately 16,000 genes that were expressed among these subsets was carried out. Consequently, 452 genes were identified that showed differential expression levels among the abovementioned subsets. When these genes were sequenced, they were found to comprise 308 novel genes and 144 known genes as the reminder. The genes were classified according to their expression patterns among the respective subsets, and grouped into seven groups.

Based on such finding, the present inventors made it possible to provide genetic information (such as nucleic acid sequence data) which would allow the detection and cloning of genes exhibiting expression patterns characteristic of stage 4s neuroblastoma. Further based on the nucleic acid sequence data, the present inventors made it possible to provide diagnostic agents and diagnostic kits which allow for methods of diagnosis for the prognosis of neuroblastoma (particularly, the classification of the progress), including determination on stage 4s neuroblastoma, upon which this invention has been completed.

Specifically, this invention provides a nucleic acid comprising one sequence selected from the group consisting of nucleic acid sequences set forth in SEQ ID NO:1 to SEQ ID NO:174 in the Sequence Listing.

The preferable nucleic acid is one that comprises a nucleic acid sequence of any one of nucleic acid sequences set forth in SEQ ID NO:1 to SEQ ID NO:14 among the nucleic acid sequences set forth in SEQ ID NO:1 to SEQ ID NO:174 in the Sequence Listing.

This invention also provides nucleic acids complementary to those nucleic acids described above.

This invention further provides nucleic acids capable of hybridizing to the nucleic acids described above or their complementary nucleic acids under stringent conditions.

This invention also provides a nucleic acid probe comprising nucleic acid (a) or nucleic acid (b) described below:

(a) a nucleic acid comprising a partial length or the full length of one sequence selected from the group consisting of nucleic acid sequences set forth in SEQ ID NO:1 to SEQ ID NO:174 in the Sequence Listing, or a nucleic acid complementary thereto;

(b) a nucleic acid capable of hybridizing under stringent conditions to a nucleic acid comprising a partial length or the full length of one sequence selected from the group consisting of nucleic acid sequences set forth in SEQ ID NO:1 to SEQ ID NO:174 in the Sequence Listing, or a nucleic acid complementary thereto.

Preferably, the nucleic acid (a) or the nucleic acid (b) is DNA.

Also preferably, the nucleic acid (a) or the nucleic acid (b) is a nucleic acid comprising one sequence selected from the group consisting of nucleic acid sequences set forth in SEQ ID NO:1 to SEQ ID NO:14 in the Sequence Listing.

This invention also provides a diagnostic agent for stage 4s neuroblastoma comprising the nucleic acid probe described above as the active ingredient.

This invention further provides a primer containing DNA (a) or DNA (b) as described below:

(a) a DNA comprising one sequence selected from the group consisting of nucleic acid sequences set forth in SEQ ID NO:175 to SEQ ID NO:1076 in the Sequence Listing, or a DNA complementary thereto;

(b) a DNA capable of hybridizing under stringent conditions to the DNA comprising one sequence selected from the group consisting of nucleic acid sequences set forth in SEQ ID NO:175 to SEQ ID NO:1076 in the Sequence Listing, or a DNA complementary thereto.

Preferably, the DNA (a) or the DNA (b) is a DNA comprising one sequence selected from the group consisting of nucleic acid sequences set forth in SEQ ID NO:175 to SEQ ID NO:202 and SEQ ID NO:519 to SEQ ID NO:540, or a DNA comprising one sequence selected from the group consisting of nucleic acid sequences set forth in SEQ ID NO:785 to SEQ ID NO:798 in the Sequence Listing.

This invention also provides a diagnostic kit for stage 4s neuroblastoma comprising one pair of the primers described above as the active component.

This invention further provides a method for determining stage 4s neuroblastoma, the method comprising detecting the presence or absence of a nucleic acid comprising one sequence selected from the group consisting of nucleic acid sequences set forth in SEQ ID NO:1 to SEQ ID NO:14 in the Sequence Listing from a clinical tissue sample of neuroblastoma.

Additionally, this invention provides a nucleic acid microarray comprising a solid phase support and a combination of plural nucleic acids each comprising a partial length- or the full length-nucleic acid comprising a nucleic acid sequence set forth in one of SEQ ID NO:1 to SEQ ID NO:174 in the Sequence Listing immobilized on the solid phase support.

This invention also provides a nucleic acid microarray comprising a solid phase support and a combination of plural nucleic acids each comprising a nucleic acid sequence set forth in one of SEQ ID NO:175 to SEQ ID NO:200, a nucleic acid sequence set forth in one of SEQ ID NO:519 to SEQ ID NO:540, or a nucleic acid sequence set forth in one of SEQ ID NO:785 to SEQ ID NO:798 immobilized on the solid phase support. Here, there may be used an arbitrary combination of plural nucleic acids comprising nucleic acid sequences having the denoted SEQ ID numbers.

BEST MODE FOR CARRYING OUT THE INVENTION

The nucleic acids (which will be referred to as "the nucleic acid(s) of this invention") derived from the gene which is expressed in neuroblastoma according to this invention (which will be referred to as "the gene(s) of this invention") including their utility, will be described in detail by referring to the preferred embodiments of the invention.

As stated above, the nucleic acids of this invention are derived from the gene of the invention and they make up the gene or are obtained from the gene by an in vivo or in vitro process. There are no limitations on the chain lengths of the nucleic acids, and herein, they will be referred to as "the nucleic acid(s) of the invention," which include nucleic acid fragments corresponding to portions of the gene. When the nucleic acid chain length is short, it can be synthesized by chemical techniques.

The term "nucleic acid(s)" as used in this specification refers to, for example, DNA or RNA, or polynucleotides derived therefrom which are active as DNA or RNA, and preferably refers to DNA or RNA. The particularly preferred nucleic acid has a DNA sequence that is identical with the human cDNA sequence disclosed in this specification or that is complementary to the sequence.

The term "hybridize under stringent conditions" as used in this specification means that two nucleic acid (or fragments thereof) hybridize to each other under the hybridization conditions as described in Sambrook, J. et al. in "Expression of cloned genes in *E. coli*", Molecular Cloning: A Laboratory Manual (1989), Cold Spring Harbor Laboratory Press, New York, USA, pp. 9.47-9.62 and pp. 11.45-11.61.

More specifically, the "stringent conditions" refers to hybridization at approximately 45° C. with 6.0×SSC, followed by washing at 50° C. with 2.0×SSC. The stringency may be selected by choosing a salt concentration in the washing step from approximately 2.0×SSC, 50° C. as low stringency to approximately 0.2×SSC, 50° C. as high stringency. Also, the temperature in the washing step may be increased from room temperature, or approximately 22° C. as low stringency conditions, to approximately 65° C. as high stringency conditions.

The term "nucleic acid(s)" as used in this specification refers to an isolated nucleic acid(s) and to a nucleic acid or a polynucleotide containing substantially no cellular substances or culture medium, if prepared by recombinant DNA techniques, or containing substantially no precursor chemical substances or other chemical substances, if prepared by chemical synthesis.

The term "favorable prognosis type" as used in this specification refers to a condition of human neuroblastoma in which the tumor exists with confinement or has become a regressing or benign sympathetic ganglion neoplasm, and is judged to have low malignancy based on N-myc or other tumor markers (TrkA, chromosomal aberration or the like) by the practicing physician. According to a preferred embodiment of the invention, neuroblastoma of the favorable prognosis type is considered a case of stage 1 or 2, with an onset age of less than one year and survival without recurrence for 5 or more years after surgery, and with no noted amplification of N-myc in the clinical tissue; however, it is not limited to such a specific case. The term "unfavorable prognosis type" as used in this specification refers to conditions of human neuroblastoma in which progression of the tumor has been observed, and it is judged to have high malignancy based on N-myc or other tumor markers by the practicing physician. According to a preferred embodiment of the invention, neuroblastoma of the unfavorable prognosis type is considered a case of stage 4, with an onset age of greater than one year, death within 3 years after surgery and noted amplification of N-myc in the clinical tissue; however, it is not limited to such a specific case.

Although stage 4s neuroblastoma is classified as the favorable prognosis type in accordance with the clinical molecular biology classification as described above, it will be treated differently from "the favorable prognosis type" for the sake of convenience in this specification.

Neuroblastoma is a tumor consisting of actual neurons, of which only two types are known in humans, and analysis of the genes expressed therein is expected to provide very useful knowledge for understanding the biology of neurons. Specifically, it is extremely difficult, and practically impossible, to obtain a site-specific homogeneous tissue from the brain or peripheral nerves. On the other hand, neuroblastoma consists of an almost homogeneous population of neurons (though tumorized) derived from peripheral sympathetic neurons, and thus offers a high possibility of obtaining homogeneous expression of neuro-related genes. Furthermore, since neuroblastoma is a type of cancer, it is characteristically pointed out that there are many important genes expressed in the immature stage of neurogenesis.

Clinically and biologically, neuroblastoma can be further distinctly classified into the favorable prognosis type and the unfavorable prognosis types. Cancer cells from neuroblastoma of the favorable prognosis type are characterized by having a very slow rate of proliferation, with spontaneous regression beginning at some point. Findings to date have confirmed that neuronal differentiation and apoptosis (neuronal cell death) occur in the spontaneous regression, and that the differentiation which occurs in the maturation stages of normal neurons and programmed cell death are phenomena very closely resembling each other. Consequently, it is highly probable that the analysis of genes expressed in such tumors will lead to obtaining important genetic information relating to neuronal differentiation and apoptosis.

The nucleic acids of this invention originating in the gene of the invention from which the useful genetic information described above can be obtained have been found in clinical tissues of stage 4s neuroblastomas (which may be referred to as "4s" hereafter). When the expression levels of these genes are compared between a clinical tissue of the favorable prognosis type (which may be abbreviated as "F(favorable)" hereafter) and a clinical tissue of the unfavorable prognosis type (which may be abbreviated as "U(unfavorable)" hereafter), the genes have the characteristics described below.

Specifically, 452 genes which were obtained in the manner described above and of which were sequenced at least partially have been classified according to their expression patterns between the respective subsets to form seven groups, which will be described in the following.

Group I

The genes belonging to this group have expression levels (4s) that are on the same order as those of UF, but are lower than those of F. These genes are further classified into subgroups, resulting in I-1, I-2 and I-3. Table 1 should be consulted on the gene expression pattern of each subgroup.

The specific clones belonging to I-1 are nbla20026 (SEQ ID NO:171), nbla20421 (SEQ ID NO:172), nbla22298 (SEQ ID NO:173), nbla22549 (SEQ ID NO:174), and nbla23020, all of which are novel genes.

The specific clones belonging to I-2 are as follows: nbla21103, nbla20146 (SEQ ID NO:137), nbla20170 (SEQ ID NO:138), nbla20216 (SEQ ID NO:139), nbla20253, nbla20549, nbla20657 (SEQ ID NO:140), nbla20688 (SEQ ID NO:141), nbla20755 (SEQ ID NO:142), nbla20835, nbla20968, nbla21013 (SEQ ID NO:143), nbla21087, nbla21172 (SEQ ID NO:144), nbla21189, nbla21200 (SEQ ID NO:145), nbla21214, nbla21255 (SEQ ID NO:146), nbla21337, nbla21344, nbla21345 (SEQ ID NO:147), nbla21410 (SEQ ID NO:148), nbla21522 (SEQ ID NO:149), nbla21631 (SEQ ID NO:150), nbla21788 (SEQ ID NO:151), nbla21897 (SEQ ID NO:152), nbla21956, nbla22116 (SEQ ID NO:153), nbla22223 (SEQ ID NO:154), nbla22228, nbla22344 (SEQ ID NO:155), nbla22351, nbla22361, nbla22474, nbla22629, nbla22939 (SEQ ID NO:156), nbla23084 (SEQ ID NO:157), nbla23103 (SEQ ID NO:158), nbla23234 (SEQ ID NO:159), nbla23300 (SEQ ID NO:160), nbla23369 (SEQ ID NO:161), nbla23436 (SEQ ID NO:162), nbla23511 (SEQ ID NO:163), nbla23664 (SEQ ID NO:164), nbla23775, nbla23860 (SEQ ID NO:165), nbla23877 (SEQ ID NO:166), nbla23998 (SEQ ID NO:167), nbla24043 (SEQ ID NO:168), nbla24182, nbla24285, nbla24402 (SEQ ID NO:169), nbla24434, nbla24460, nbla24762, nbla24821 (SEQ ID NO:170), nbla24893, nbla24973, and nbla24986, all of which are novel genes; and nbla20279, nbla20687, nbla20924, nbla21168, nbla21303, nbla21483, nbla21838, nbla21917, nbla22099, nbla22438, nbla23111, nbla23208, nbla24118, nbla24279, nbla24771, and nbla24871, all of which are known genes.

The specific clones belonging to I-3 are as follows: nbla20084 (SEQ ID NO:129), nbla21081 (SEQ ID NO:130), nbla21420 (SEQ ID NO:131), nbla21761, nbla22452 (SEQ ID NO:132), nbla22595 (SEQ ID NO:133), nbla22676 (SEQ ID NO:134), nbla22909 (SEQ ID NO:135), nbla23456, nbla24297, nbla24435 (SEQ ID NO:136), and nbla24719, all of which are novel genes; and nbla20117, nbla20238, nbla20904, nbla23293, nbla23297, nbla23311, nbla23589, nbla23629, nbla23862, nbla2413, and nbla24761, all of which are known genes.

Group II

The genes belonging to this group have expression levels (4s) that are on the same order as those of F, but are higher than those of UF. These genes are further classified into subgroups, resulting in II-1, II-2 and II-3. Table 1 should be consulted on the gene expression pattern of each subgroup.

The specific clones belonging to II-1 are as follows: nbla20365 (SEQ ID NO:117), nbla20378 (SEQ ID NO:118), nbla20511 (SEQ ID NO:119), nbla21039 (SEQ ID NO:120), nbla21107 (SEQ ID NO:121), nbla21367 (SEQ ID NO:122), nbla21790 (SEQ ID NO:123), nbla21855, nbla22253 (SEQ ID NO:124), nbla22355 (SEQ ID NO:125), nbla22704, nbla22832 (SEQ ID NO:126), nbla23394, nbla23512, nbla23755 (SEQ ID NO:127), nbla24084, nbla24376, and nbla24549 (SEQ ID NO:128), all of which are novel genes; and nbla20624, nbla22029, nbla22424, nbla22594 and nbla22622, all of which are known genes.

The specific clones belonging to II-2 are as follows: nbla20001 (SEQ ID NO:58), nbla20083 (SEQ ID NO:59), nbla20125, nbla20182 (SEQ ID NO:60), nbla20231, nbla20248 (SEQ ID NO:61), nbla20250 (SEQ ID NO:62), nbla20268, nbla20330 (SEQ ID NO:63), nbla20395, nbla23973, nbla23983 (SEQ ID NO:64), nbla24041, nbla24082, nbla24104, nbla24111 (SEQ ID NO:65), nbla24142 (SEQ ID NO:66), nbla24157 (SEQ ID NO:67), nbla24230 (SEQ ID NO:68), nbla24239, nbla20541 (SEQ ID NO:69), nbla20555 (SEQ ID NO:70), nbla20638, nbla20645 (SEQ ID NO:71), nbla20713 (SEQ ID NO:72), nbla20765, nbla20789, nbla20792, nbla20798, nbla21024, nbla24250 (SEQ ID NO:73), nbla24254 (SEQ ID NO:74), nbla24327 (SEQ ID NO:75), nbla24363, nbla24510 (SEQ ID NO:76), nbla24554 (SEQ ID NO:77), nbla24604 (SEQ ID NO:78), nbla24622, nbla24646, nbla24672, nbla21037 (SEQ ID NO:79), nbla21077, nbla21089, nbla21130, nbla21161 (SEQ ID NO:80), nbla21170 (SEQ ID NO:81), nbla21198 (SEQ ID NO:82), nbla21266, nbla21298 (SEQ ID NO:83), nbla21379 (SEQ ID NO:84), nbla24705 (SEQ ID NO:85), nbla24709, nbla24748, nbla24831, nbla24972, nbla21385 (SEQ ID NO:86), nbla21413, nbla21416 (SEQ ID NO:87), nbla21520, nbla21599 (SEQ ID NO:88), nbla21681 (SEQ ID NO:89), nbla21878 (SEQ ID NO:90), nbla21922 (SEQ ID NO:91), nbla21936, nbla22004-2 (SEQ ID NO:92), nbla22004-1 (SEQ ID NO:93), nbla22028, nbla22085 (SEQ ID NO:94), nbla22093, nbla22119 (SEQ ID NO:95), nbla22149 (SEQ ID NO:96), nbla22161 (SEQ ID NO:97), nbla22218, nbla22252 (SEQ ID NO:98), nbla22347 (SEQ ID NO:99), nbla22352 (SEQ ID NO:100), nbla22394 (SEQ ID NO:101), nbla22423 (SEQ ID NO:102), nbla22439 (SEQ ID NO:103), nbla22451, nbla22455, nbla22464, nbla22465, nbla22487, nbla22633 (SEQ ID NO:104), nbla22669, nbla22698 (SEQ ID NO:105), nbla22726, nbla22886, nbla22896 (SEQ ID NO:106), nbla23012, nbla23038, nbla23167 (SEQ ID NO:107), nbla23339 (SEQ ID NO:108), nbla23352 (SEQ ID NO:109), nbla23575 (SEQ ID NO:110), 23592 (SEQ ID NO:111), nbla23601 (SEQ ID NO:112), nbla23630 (SEQ ID NO:113), nbla23718, nbla23719, nbla23754 (SEQ ID NO:114), nbla23892 (SEQ ID NO:115), nbla23951, and nbla23956 (SEQ ID NO:116), all of which are novel genes; and nbla20393, nbla20423, nbla20510, nbla20833, nbla20931, nbla20943, nbla21258, nbla21268, nbla21273, nbla21412, nbla21578, nbla21614, nbla21624, nbla21655, nbla21670, nbla21787, nbla21954, nbla21979, nbla22043, nbla22137, nbla22192, nbla22325, nbla22327, nbla22337, nbla22482, nbla22763, nbla22788, nbla22839, nbla22851, nbla22935, nbla22937, nbla23238, nbla23327, nbla23360, nbla23519, nbla23553, nbla23554, nbla23683, nbla23812, nbla23823, nbla23849, nbla23882, nbla23910, nbla24064, nbla24405, nbla24897, and nbla24913, all of which are known genes.

The specific clones belonging to II-3 are as follows: nbla20134, nbla20181, nbla20264 (SEQ ID NO:31), nbla20269 (SEQ ID NO:32), nbla20276, nbla20406 (SEQ ID NO:33), nbla20709, nbla20782, nbla20788, nbla20949 (SEQ ID NO:34), nbla21046, nbla21122, nbla21211, nbla21233, nbla21251 (SEQ ID NO:35), nbla21334 (SEQ ID NO:36), nbla21356 (SEQ ID NO:37), nbla21375, nbla21418 (SEQ ID NO:38), nbla21480 (SEQ ID NO:39), nbla21509 (SEQ ID NO:40), nbla21524, nbla21527 (SEQ ID NO:41), nbla21551 (SEQ ID NO:42), nbla21735 (SEQ ID NO:43), nbla21843, nbla21934, nbla22153, nbla22247 (SEQ ID NO:44), nbla22382, nbla22477 (SEQ ID NO:45), nbla22571, nbla22639 (SEQ ID NO:46), nbla22789, nbla23060, nbla23174 (SEQ ID NO:47), nbla23198 (SEQ ID NO:48), nbla23218, nbla23328 (SEQ ID NO:49), nbla23420 (SEQ ID NO:50), nbla23483 (SEQ ID NO:51), nbla23545, nbla23653, nbla23666, nbla23760, nbla23808 (SEQ ID NO:52), nbla23830, nbla23851 (SEQ ID NO:53), nbla23942, nbla24011 (SEQ ID NO:54), nbla24131, nbla24235 (SEQ ID NO:55), nbla24556 (SEQ ID NO:56), nbla24800 (SEQ ID NO:57), and nbla24908, all of which are novel genes; and nbla20133, nbla20263, nbla20723, nbla20748, nbla20915, nbla21016, nbla21034, nbla21067, nbla21167, nbla21319, nbla21331, nbla21516, nbla21682, nbla21691, nbla21822, nbla21976-2, nbla21977, nbla22159, nbla22168, 22215-1, nbla22244, nbla22263, nbla22548, nbla23033, nbla23231, nbla23284, nbla23329-1, nbla23384, nbla23556, nbla23674, nbla23879-2, nbla24098, nbla24329, nbla24334, nbla24439-1, nbla24443, nbla24507, nbla24836, nbla24958, and nbla24989, all of which are known genes.

Group III

The genes belonging to this group have expression levels (4s) that are on the same order as those of F, but are lower than those of UF. These genes are further classified into subgroups, resulting in III-1, III-2 and III-3. Table 1 should be consulted on the gene expression pattern of each subgroup.

The specific clones belonging to III-1 are nbla20874 (novel gene) and nbla23262 (known gene).

The specific clones belonging to III-2 are as follows: nbla20604, nbla21226, nbla21908 (SEQ ID NO:27), nbla21928, nbla22027 (SEQ ID NO:28), nbla22082 (SEQ ID NO:29), nbla22643, nbla23303(SEQ ID NO:30), nbla23649, and nbla24468, all of which are novel genes; and nbla20141, nbla20446, nbla21538, nbla21558, nbla21623, nbla21969, nbla22219, nbla23272, nbla23307 and nbla24117, all of which are known genes.

The specific clones belonging to III-3 are as follows: nbla20578 (SEQ ID NO:26), and nbla21212, both of which are novel genes; and nbla23478, nbla23896 and nbla24920, all of which are known genes.

Group IV

The genes belonging to this group have expression levels (4s) that are on the same order as those of UF, but are higher than those of F (F<4s=UF). The specific genes belonging to this group are nbla23899 (SEQ ID NO:25) and nbla24526, both of which are novel genes.

Group V

The genes belonging to this group have expression levels (4s) that are lower than those of F, but are higher than those of UF. These genes are further classified into subgroups, resulting in V-1, V-2, V-3, V-4 and V-5. Table 1 should be consulted on the gene expression pattern of each subgroup.

The specific clone belonging to V-1 is nbla22031 (known gene). The specific clone belonging to V-2 is nbla22305 (known gene).

The specific clones belonging to V-3 are as follows: nbla20123 (SEQ ID NO:17), nbla20382 (SEQ ID NO:18), nbla20660 (SEQ ID NO:19), nbla20666 (SEQ ID NO:20), nbla21239 (SEQ ID NO:21), nbla21729 (SEQ ID NO:22), nbla21831 (SEQ ID NO:23), nbla22826 (SEQ ID NO:24), and nbla24521, all of which are novel genes; and nbla20235 and nbla22607, both of which are known genes.

The specific clones belonging to V-4 are nbla20787 (SEQ ID NO:15), nbla22284 (SEQ ID NO:16) and nbla24756, all of which are novel genes.

The specific clones belonging to V-5 are nbla24348 and nbla24686, both of which are novel genes.

Group VI

The genes belonging to this group have expression levels (4s) that are lower than either of F and UF, or are higher than either of F and UF. These genes are further classified into subgroups, resulting in VI-1, VI-2, VI-3, VI-4, VI-5, VI-6, VI-7 and VI-8. Table 1 should be consulted on the gene expression pattern of each subgroup.

The specific clones belonging to VI-1 are nbla21297 (SEQ ID NO:14) (novel gene) and nbla22443 (known gene).

The specific clones belonging to VI-2 are as follows: nbla20211, nbla20469, nbla21250, nbla22182 (SEQ ID NO:12), nbla22761, nbla23256 (SEQ ID NO:13), nbla23631, nbla23711, nbla24532, and nbla24951, all of which are novel genes; and nbla21750, nbla22129, nbla22808, nbla23064, and nbla23358, all of which are known genes.

The specific clone belonging to VI-3 is nbla20226 (SEQ ID NO:11) (novel gene).

The specific clones belonging to VI-4 are nbla21650 (SEQ ID NO:7), nbla22094 (SEQ ID NO:8), nbla22739 (SEQ ID NO:9), and nbla23525 (SEQ ID NO:10), all of which are novel genes.

The specific clones belonging to VI-5 are nbla23701 (SEQ ID NO:5) and nbla23890 (SEQ ID NO:6), both of which are novel genes.

The specific clone belonging to VI-6 is nbla20087 (known gene).

The specific clones belonging to VI-7 are nbla22689 (SEQ ID NO:2), nbla22968, nbla24079, nbla24135 (SEQ ID NO:3), and nbla24350 (SEQ ID NO:4), all of which are novel genes.

The specific clone belonging to VI-8 is nbla22256 (novel gene).

Group VII

The gene belonging to this group (only one) is expressed only in 4s. The specific clone is nbla22420 (SEQ ID NO:1) (novel gene).

The gene groups have been divided into novel genes and known genes with respect to each group. A summary is shown in Table 1.

TABLE 1

| Group | Expression pattern | Novel genes | Known genes | Total |
| --- | --- | --- | --- | --- |
| I-1 | F >> 4s = UF | 5 | 0 | 5 |
| I-2 | F > 4s = UF | 59 | 16 | 75 |
| I-3 | F ≧ 4s = UF | 12 | 11 | 23 |
| II-1 | F = 4s >> UF | 18 | 5 | 23 |
| II-2 | F = 4s > UF | 105 | 47 | 152 |
| II-3 | F = 4s ≧ UF | 55 | 40 | 95 |
| III-1 | F = 4s << UF | 1 | 1 | 2 |
| III-2 | F = 4s < UF | 10 | 10 | 20 |

TABLE 1-continued

| Group | Expression pattern | Novel genes | Known genes | Total |
|---|---|---|---|---|
| III-3 | F = 4s < UF | 2 | 3 | 5 |
| IV | F < 4s = UF | 2 | 0 | 2 |
| V-1 | F > 4s >> UF | 0 | 1 | 1 |
| V-2 | F ≧ 4s >> UF | 0 | 1 | 1 |
| V-3 | F > 4s > UF | 9 | 2 | 11 |
| V-4 | F ≧ 4s > UF | 3 | 0 | 3 |
| V-5 | F ≧ 4s ≧ UF | 2 | 0 | 2 |
| VI-1 | F >> 4s < UF | 1 | 1 | 2 |
| VI-2 | F > 4s < UF | 10 | 5 | 15 |
| VI-3 | F > 4s ≦ UF | 1 | 0 | 1 |
| VI-4 | F ≧ 4s ≦ UF | 4 | 0 | 4 |
| VI-5 | F < 4s >> UF | 2 | 0 | 2 |
| VI-6 | F ≦ 4s >> UF | 0 | 1 | 1 |
| VI-7 | F < 4s > UF | 5 | 0 | 5 |
| VI-8 | F ≦ 4s ≧ UF | 1 | 0 | 1 |
| VII | 4s only | 1 | 0 | 1 |
| Total clone number | | 308 | 144 | 452 |

In the table and the above classification, "=" shows that the gene expression levels are nearly equal between the subsets.

Specifically, with respect to a group of genes belonging to group VI, when their expression levels in the stage 4s neuroblastoma and the expression levels of the same genes in clinical samples of the neuroblastomas of the favorable and unfavorable prognosis types are compared, they are specific in the stage 4s neuroblastoma: that is, their expression levels are significantly higher or lower than in either type of neuroblastomas. Therefore, if the presence of at least one of those genes is detected in a clinical tissue sample, it can be judged that there is a high probability of the sample being stage 4s neuroblastoma.

The gene belonging to Group VII is detected only in a clinical tissue of stage 4s neuroblastoma. Therefore, if the presence of this gene is detected in a clinical tissue sample, it can be judged that there is a high probability of the sample being stage 4s neuroblastoma.

Further, with respect to a group of genes belonging to one of the remaining groups, when their expression levels in the stage 4s neuroblastoma and the expression levels of the same genes in clinical samples of the neuroblastomas of the favorable and unfavorable prognosis types are compared, the expression patterns as described above can be found. Therefore, if plural expression patterns of those genes are detected and analyzed, it can be judged as to whether the clinical tissue sample to be assayed is stage 4s neuroblastoma. Particularly, when the nucleic acids of this invention are used for this purpose, it is preferred that a nucleic acid microarray (which will be described below) be constructed and provided for determining neuroblastomas.

Thus, the nucleic acids of this invention are useful as tumor markers to diagnose the favorable or unfavorable prognosis of neuroblastoma. Specifically, this invention will allow for providing various genetic information on or relating to the prognosis of human neuroblastoma through the following means.

(1) Probes for Use in Hybridization

According to one embodiment of this invention, the nucleic acid of the invention can be used as a probe (the nucleic acid probe of this invention) for hybridization to detect the gene of the invention expressed in neuroblastoma. The nucleic acid of this invention can also be used as a probe for hybridization in order to determine gene expression in various tumors and normal tissues, to identify the distribution of the gene expression.

When the nucleic acid of this invention is used as a probe for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization methods, the nucleic acid of this invention can be used as a probe for Northern hybridization to measure the length of mRNA or to quantitatively detect gene expression in a clinical tissue sample to be assayed.

As another application example, the nucleic acid of this invention can be used as a probe for Southern hybridization to detect the presence or absence of a DNA sequence in the genomic DNA of a clinical tissue sample to be assayed.

As still another application example, the nucleic acid of this invention can also be used as a probe for the FISH method to identify the location of a gene of the invention on a chromosome.

As a further application example, the nucleic acid of this invention can also be used as a probe for the ISH method to identify the tissue distribution of expression of a gene of the invention.

When the nucleic acid of this invention is used as a probe for hybridization, a base length of at least 20 is necessary; and among the nucleic acids of this invention, a nucleic acid comprising 20 or more contiguous bases is preferably used. More preferably, the nucleic acid comprising 40 or more contiguous bases is used and most preferably a nucleic acid comprising 60 or more contiguous bases is used. Further, there may be used a nucleic acid comprising the full-length of any of the nucleic acid sequences set forth in SEQ ID NO:1 to SEQ ID NO:174 in the Sequence Listing.

The nucleic acid probe techniques in the various hybridization methods described above are well known to one skilled in the art, and for example, the conditions suitable for hybridization between a probe of this invention with each individual base length and the target polynucleotide may be readily determined. In order to obtain hybridization conditions optimal to probes containing varying base lengths, Sambrook et al. "Molecular Cloning: A Laboratory Manual" (loc. cit.) may be consulted and followed for such manipulations which are well known to one skilled in the art.

The probe of this invention may preferably be labeled for use in an easily detectable fashion. The detectable label may be any type and any element or compound which can be detected either visually or using devices. As commonly used detectable labels, there may be mentioned radioactive isotopes, avidin and biotin and fluorescent substances (FITC or Rhodamins). The radioactive isotopes are $^{32}P$, $^{14}C$, $^{125}I$, $^{3}H$, $^{35}S$ etc. Biotin-labeled nucleotides may be incorporated into nucleic acids by nick translation, or chemical or enzymatic means. The biotin-labeled probes are detected after hybridization using labeling means such as avidin/streptavidin, fluorescent labels, enzymes, gold colloidal complexes or the like. The nucleic acid probe of this invention may also be labeled by binding with a protein. For this purpose, a radioactive or fluorescent histone single-stranded binding protein may be used, for example. In this manner, a suitably labeled probe constitutes a diagnostic agent of this invention.

(2) Primers for Use in PCR

In order to detect the gene of this invention other than through the hybridization, primers can be designed after any nucleic acid (DNA) sequence contained in the nucleic acid of the invention and the polymerase chain reaction (PCR) method can be used. For example, mRNA may be extracted from a clinical tissue sample to be assayed, and the gene expression can be semi-quantitatively measured by RT-PCR. Such method may be carried out by a method well known to one skilled in the art. For example, "Molecular Cloning: A Laboratory Manual," (loc. cit.) and or Idenshibyo Nyumon [Introduction to Genetic Diseases] (Takahisa, S.: Nankodo Publishing) may be consulted.

When the nucleic acid (DNA) of this invention is used as a PCR primer (i.e., the primer of the invention), a base length of 10 to 60 is necessary; and among portions of the nucleic acid sequences according to the invention, the nucleic acid having 10 to 60 contiguous bases is preferably used. More preferably, one having 15 to 30 bases is used. Generally, a primer sequence with a GC content of 40-60% is preferred. Also, there should preferably be no difference in the Tm values of the two primers used for amplification. Desirably, the primers do not anneal at their 3'-ends and do not adopt any secondary structures within the primers.

(3) Gene Screening

The nucleic acid of this invention can also be used to detect the expression (or the distribution) of a gene of the invention which is expressed in various tissues or cells, non-limiting to neuroblastoma. This can be accomplished, for example, by using the nucleic acid of this invention as a probe for hybridization or as a primer for PCR as described above.

The expression distribution of the gene can also be detected using a DNA chip, a nucleic acid microarray or the like. That is, the nucleic acid of the invention may be directly attached to the chip or array. There is known a method by which nucleic acids (DNA) are spotted to a substrate for the purpose of attaching them to a chip or array by using a high precision dispenser (see, for example, U.S. Pat. No. 5,807,522). mRNA extracted from a clinical tissue sample may be labeled with a fluorescent substance or the like, hybridized thereto, and an analysis can be made of the type of tissue cells with high expression of the gene. The DNA attached to the chip or the array may be the reaction product of PCR using the nucleic acid or its fragment of this invention. As an alternative method, the nucleic acid fragment of this invention (DNA fragment) may be directly synthesized on a substrate to form a DNA chip or a DNA array (see, for example, U.S. Pat. No. 5,424,186).

(4) DNA Cloning

The nucleic acid of this invention can be used for cloning a gene which is expressed in human neuroblastoma. For example, by using the nucleic acid of the invention as a probe for Northern hybridization or colony hybridization, or as a primer for PCR, cloning of a gene containing the nucleic acid of the invention is possible. The genes capable of being cloned include, among others, genes displaying differential expression levels between neuroblastomas of the unfavorable prognosis type and neuroblastomas of the unfavorable prognosis type, genes expressed in stage 4s neuroblastoma, genes displaying expression in a pattern different from the expression patterns in other tissues or cancer cells, genes expressed in a cell cycle dependent manner, genes induced by nerve differentiation, and genes whose expression is regulated by oncogenes or cancer suppressor genes.

(5) Methods for Diagnosing Tumor Prognosis and Tumor Markers to be Used Therefore As mentioned above, expression of the gene of this invention was found in stage 4s neuroblastoma (including neuroblastomas of the favorable and unfavorable prognosis types). Therefore, the nucleic acid of this invention can be used as a probe for hybridization, or as a primer for PCR to investigate the expression pattern of the gene in a clinical tissue sample to be assayed taken from the subject, which enables the diagnosis for prognosis (i.e., determining stage 4s neuroblastoma). The methods of detecting the gene include Northern blotting hybridization, in situ hybridization and RT-PCR, as mentioned above among others.

When hybridization is employed, the amount of the nucleic acid hybridizing to the nucleic acid probe mentioned above in a clinical tissue sample to be assayed is compared with the control sample (e.g., clinical tissue samples from neuroblastomas of the favorable and unfavorable prognosis types) and the gene expression is determined. For the respective nucleic acids used to detect the gene expression patterns, their expression patterns may then be, for example, compared with those listed in Table 1 and analyzed to enable the diagnosis for prognosis. For this purpose, the nucleic acid microarray mentioned above may desirably be used. When RT-PCR is employed instead, mRNA is extracted from the sample and reverse-transcribed into DNA, amplification is performed using the aforementioned primers, and the gene expression is semi-quantitatively measured. Similarly to the manner mentioned above, the diagnosis for prognosis can be made. For this purpose, it is preferred to utilize a diagnostic kit containing a pair of the primers as essential components. In addition to the primer components, the diagnostic kit also includes known components such as PCR buffer, detergent solution and enzymes.

(6) Antisense Oligonucleotides

According to another embodiment of this invention, there are provided antisense oligonucleotides to the nucleic acids of the invention. The antisense oligonucleotides are capable of hybridizing to the nucleic acids of this invention, and include antisense DNAs and antisense RNAs. Antisense DNA inhibits transcription of mRNA from DNA, while antisense RNA inhibits translation of mRNA. These antisense oligonucleotides may be synthesized using an automated synthesizer or by PCR using the nucleic acids of this invention as templates. The antisense oligonucleotides also encompass antisense oligonucleotide derivatives having improved binding affinity for DNA or mRNA, tissue selectivity, cell permeability, nuclease resistance and intracellular stability. These derivatives may be synthesized using the antisense technology known in the art.

Antisense oligonucleotides having sequences complementary to the sequences near the translation initiation codon of the mRNA, those of the ribosome-binding site, and those of the capping site or the splicing site are capable of inhibiting synthesis of the RNA, and therefore, will exhibit a particularly notable inhibitory effect on gene expression. This invention, therefore, encompasses such antisense oligonucleotides.

(7) Gene Therapy

According to a further embodiment of this invention, there are provided nucleic acid sequences encoding the therapeutic genes to be used in gene therapy. Thus, the nucleic acid of this invention can be transferred into a vector for use in gene transportation, whereby the transgene (i.e., the gene of the invention) can be expressed by an arbitrary expression promoter and can be used for the gene therapy.

1. Vectors

The transferable viral vectors may be prepared from DNA or RNA viruses. Such vectors may be any type of viral vectors from an MoMLV vector, a herpes virus vector, an Adenovirus vector, an AAV vector, a HIV vector, a SIV vector, a Sendai virus vector and the like. One or more proteins among the constituent protein group of a viral vector are substituted by the constituent proteins of a different species of virus, or alternatively a part of the nucleic acid sequence constituting genetic information is substituted by the nucleic acid sequence of a different species of virus to form a viral vector of the pseudo-type, which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science vol. 272, p. 263, 1996). Further, viruses having a host spectrum other than humans are usable as the viral vector insofar as they are efficacious. As for the vectors other than those of viral origin, there may be used complexes of calcium phosphate and nucleic acid, ribosomes, cation-lipid complexes, Sendai virus liposomes, polymer carriers having polycation as the backbone main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SR α, a heat shock protein, and an elongation factor; chimera type promoters such as a CAG promoter; and the promoters whose expression can be induced by tetracyclines, steroids and the like.

3. Drugs

The drugs to be used in the gene therapy may be prepared as a recombinant viral vector containing the therapeutic gene that is designed for therapeutic purposes as described above. More specifically, a recombinant virus vector containing the gene of this invention may be prepared by dissolving it in an appropriate solvent such as water, physiological saline or an isotonized buffer solution. Here, polyethylene glycol, glucose, various amino acids, collagen, albumin or the like can be then added as protective materials to form preparations.

4. Administration Method and Dosage

There are no particular limitations on the method of administrating the drug mentioned above to humans. For example, parental administration, including injection is preferably carried out. The use level of the drug varies depending on the method of use, the purpose of use, etc.; and one skilled in the art can easily select as appropriate and optimize it. In the case of injection, for example, the daily dosage is preferably administered at about 0.1 μg/kg to 1,000 mg/kg per day, and more preferably at about 1 μg/kg to 100 mg/kg per day.

This invention will be described hereafter in greater detail by way of the examples; however, the technical scope of the invention will not be restricted to those examples.

EXAMPLES

The invention will be described hereafter based on the examples more concretely; however, the invention will not be restricted to the examples described below.

Preparation Example 1

Construction of cDNA Library from Neuroblastoma

1. Obtaining Samples

Clinical tissue samples of human neuroblastoma (stage 4s) were quasi-aseptically frozen immediately after surgical extraction and then preserved at −80° C.

2. Preparation of mRNA

A 2-3 g portion of the sample described in 1 was treated with a Total RNA Extraction Kit (QIAGEN Inc.) and the total RNA was extracted. The extracted total RNA was purified using an oligo dT cellulose column (Collaborative Research, Inc.) to obtain a pool of mRNA with a polyA structure. Following the procedure described below, a cDNA library was prepared according to the oligo capping method (Y. Suzuki et al., Gene, U.S.A., Vol. 200, pp. 149-156, 1997).

3. Dephosphorylation of mRNA

A 100-200 μg portion of the mRNA pool prepared in 2 above was dissolved in 67.3 μl of sterile ultra-purified water containing 0.1% diethyl pyrocarbonate (DEPC) (DEPC—$H_2O$), and then 20 μl of 5×BAP buffer [Tris-HCl (500 mM, pH=7.0)/mercaptoethanol (50 mM)], 2.7 μl of RNasin (40 unit/μl: Promega Inc.) and 10 μl of BAP (0.25 unit/μl, bacteria-derived alkali phosphatase: Takara Shuzo Co. Ltd.) were added. The mixture was reacted at 37° C. for 1 hour to effect dephosphorylation of the 5' end of the mRNA. This was followed by phenol/chloroform treatment twice, and finally by ethanol precipitation to obtain a purified dephosphorylated mRNA pool.

4. Decapping of Dephosphorylated mRNA

The total amount of the dephosphorylated mRNA pool prepared in 3 above was dissolved in 75.3 μl of sterile ultra-purified water containing 0.1% DEPC, and then 20 μl of 5×TAP buffer [sodium acetate (250 mM, pH=5.5)/mercaptoethanol (50 mM), EDTA (5 mM, pH=8.0)], 2.7 μl of RNasin (40 unit/μl) and 2 μl of TAP (tobacco acid pyrophosphatase: 20 unit/μl) were added. The mixture was reacted at 37° C. for 1 hour to effect decapping treatment of the 5' end of the dephosphorylated mRNA. The dephosphorylated mRNA of incomplete length with no capped structure remained without decapping, and with the 5' end dephosphorylated. This was followed by phenol/chloroform treatment and ethanol precipitation to obtain a purified decapped mRNA pool.

5. Preparation of Oligo-Capped mRNA

The total amount of the decapped mRNA pool prepared in 4 above was dissolved in 11 μl of sterile ultra-purified water containing 0.1% DEPC, and then 4 μl of 5'-oligo RNA (5'-AGCAUCGAGUCGGCCUUGGCCUACUGG-3': SEQ ID NO:1079; 100 ng/μl), 10 μl of 10×ligation buffer [Tris-HCl (500 mM, pH=7.0)/mercaptoethanol (100 mM)], 10 μl of magnesium chloride (50 mM), 2.5 μl of ATP (24 mM), 2.5 μl of RNasin (40 unit/μl), 10 μl of T4 RNA ligase (25 unit/μl: Takara Shuzo Co. Ltd.) and 50 μl of polyethylene glycol (50% w/v, PEG8000: Sigma Corporation) were added. The mixture was reacted at 20° C. for 3 hours for ligation of the 5'-oligo RNA to the 5' end of the decapped mRNA. The dephosphorylated mRNA of incomplete length with no capped structure resulted in no ligation to the 5'-oligo RNA. This was followed by phenol/chloroform treatment and ethanol precipitation to obtain a purified oligo-capped mRNA pool.

6. Removal of DNA from Oligo-Capped mRNA

The oligo-capped mRNA pool prepared in 6 above was dissolved in 70.3 μl of sterile ultra-purified water containing 0.1% DEPC, and then 4 μl of Tris-HCl (1 M, pH=7.0), 5.0 μl of DTT (0.1 M), 16 μl of magnesium chloride (50 mM), 2.7 μl of RNasin (40 unit/μl) and 2 μl of DNaseI (5 unit/μl: Takara Shuzo Co. Ltd.) were added. The mixture was reacted at 37° C. for 10 minutes to digest the excess DNA. This was followed by phenol/chloroform treatment and ethanol precipitation and column purification (S-400HR: Pharmacia Biotech Inc.), to obtain a purified DNA(−) oligo-capped mRNA pool.

7. Preparation of 1st Strand cDNA

The DNA(−) oligo-capped mRNA pool prepared in 7 above was reverse-transcribed using Super Script II (kit manufactured by Life Tech Oriental, Inc.) to obtain a pool of 1st strand cDNA.

The pool of DNA(−) oligo-capped mRNA was dissolved in 21 μl of sterile distilled water, and then 10 μl of 10×First Strand buffer (kit accessory), 8 μl of dNTP mix (5 mM, kit accessory), 6 μl of DTT (0.1 M, kit accessory), 2.5 μl of oligo-dT adapter primer (5 pmol/μl, 5'-GCGGCTGAA-GACGGCCTATGTGGCCTTTTTTTTTTTTTTTTT-3': SEQ ID NO:1080), 2.0 μl of RNasin (40 unit/μl) and 2 μl of Super Script II RTase (kit accessory) were added. The mixture was reacted at 42° C. for 3 hours to effect reverse transcription. This was followed by phenol/chloroform treatment, alkali treatment and neutralization treatment to digest all the RNA and purification was carried out by ethanol precipitation.

8. Preparation of 2nd Strand cDNA

The 1st strand cDNA pool prepared in 7 above was subjected to PCR amplification using Gene Amp (kit manufactured by Perkin Elmer Inc.). The pool of 1st strand cDNA was dissolved in 52.4 μl of sterile distilled water, and then 30 μl of 3.3× Reaction buffer (kit accessory), 8 μl of dNTP mix (2.5 mM, kit accessory), 4.4 μl of magnesium acetate (25 mM, kit accessory), 1.6 μl of Primer F (10 pmol/μl, 5'-AGCATC-GAGTCGGCCTTGTTG-3': SEQ ID NO:1081), 1.6 μl of Primer R (10 pmol/μl, 5'-GCGCTGAAGACGGCCTATGT-3': SEQ ID NO:1082) and 2 μl of rTth (kit accessory) were added. Mineral oil (100 μl) was gently added to the mixture and overlayed thereon. After denaturing the reaction solution at 94° C. for 5 minutes, a cycle of 94° C. for 1 minute, 52° C. for 1 minute and 72° C. for 10 minutes was repeated 12 times, and then the solution was allowed to stand at 72° C. for 10 minutes to complete the PCR reaction. This was followed by purification with phenol/chloroform treatment and ethanol precipitation to obtain a 2nd strand cDNA pool.

9. SfiI Treatment of 2nd Strand cDNA

The 2nd strand cDNA pool prepared in 8 above was dissolved in 87 μl of sterile distilled water, and then 10×NEB buffer (NEB Inc.), 100×BSA (bovine serum albumin manufactured by NEB Inc.) and 2 μl of SfiI (restriction endonuclease, 20 unit/μl, manufactured by NEB Inc.) were added. The mixture was reacted overnight at 50° C. to effect SfiI restriction endonuclease treatment. This was followed by purification with phenol/chloroform treatment and ethanol precipitation to obtain a pool of cDNA which had been SfiI-treated at both ends.

10. Size Fractionation of SfiI-Treated cDNA

The SfiI-treated cDNA pool prepared in 9 above was electrophoresed on 1% agarose gel and a fraction with >2 kb was purified using Geneclean II (Bio101 Inc.). The purified cDNA pool was dissolved in 100 μl of sterile distilled water and allowed to stand at 37° C. for 6 hours. This was followed by purification with phenol/chloroform treatment and ethanol precipitation to obtain a long-chain cDNA pool.

11. cDNA Library

The long-chain cDNA pool prepared in 10 above was ligated into the cloning vector pME18S-FL3 (provided by Prof Sumio Kanno of the Institute of Medical Science, Tokyo University) using a DNA Ligation Kit ver.1 (kit manufactured by Takara Shuzo Co. Ltd.). The long-chain cDNA pool was dissolved in 8 μl of sterile distilled water, and then 1 μl of pME18S-FL3 pretreated with restriction endonuclease DraIII, 80 μl of Solution A (kit accessory) and 10 μl of Solution B (kit accessory) were added and reaction was conducted at 16° C. for 3 hours. This was followed by purification with phenol/chloroform treatment and ethanol precipitation to obtain a cDNA library.

Example 1

Transformation into *E. coli*

1. Cloning

The cDNA library prepared in Preparation Example 1, Item 12 above was used for transformation into *E. Coli* (TOP-10: Invitrogen Corporation). Specifically, the cDNA library was dissolved in 10 μl of sterile distilled water and mixed with TOP-10. The mixture was then incubated on ice for 30 minutes, at 40° C. for 1 minute and on ice for 5 minutes. After adding 500 μl of SOB medium, shake culturing was performed at 37° C. for 60 minutes. Appropriate amounts thereof were seeded onto an ampicillin-containing agar media and culturing was continued at 37° C. for 24 hours to obtain *E. Coli* clones. There, 5075 clones were picked up randomly.

2. Preservation of *E. coli* Clones (Preparation of Glycerol Stock)

The *E. coli* clones on agar media obtained in 1 above were collected with toothpick and suspended in 120 μl of LB medium prepared in a 96-well plate. The 96-well plate was then allowed to stand overnight at 37° C. for culturing of the *E. coli*. 60% Glycerol solution (72 μl) was then added and preserved at −20° C. (glycerol stock).

Example 2

Nucleic Acid Sequencing

1. Preparation of Plasmid

The glycerol stock (10 μl) prepared in Example 1, Item 2 above was transferred to a 15 ml-centrifugation tube, and then 3 ml of LB medium and 50 μg/ml of ampicillin were added and shaking was carried out overnight at 37° C. for culturing of the *E. coli*. A QIAprep Spin Miniprep Kit (QIAGEN Inc.) was then used to extract and purify a plasmid DNA from the *E. coli*.

2. Analysis of Both End Sequences

Both end sequences of the plasmid DNA prepared in 1 above were determined using a DNA Sequencing Kit (kit manufactured by ABI). There were combined 600 ng of plasmid DNA, 8 μl of premix (kit accessory) and 3.2 μmol of primers, and sterile distilled water was added to a total of 20 μl. After denaturing the mixture at 96° C. for 2 minutes, a cycle of 96° C. for 10 seconds, 50° C. for 5 seconds and 60° C. for 4 minutes was repeated 25 times for reaction. The product was then purified by ethanol precipitation. Sequence determination was carried out by polyacrylamide gel electrophoresis under denaturing conditions, using ABI377 (ABI).

An internet-mediated DNA sequence homology search was conducted for DNA sequence data obtained from the both end-sequence analysis in Example 2. The search was conducted using the BLAST database of the NCBI (National Center of Biotecbnology Information. As a result of the homology search, approximately 2,700 genes were identified. These genes were classified and repeat sequences were eliminated using a RepeatMasker software to obtain 1598 genes. Out of the genes, 963 genes were novel and 635 genes were known.

With respect to 308 of novel genes among those genes, those which could be sequenced are shown in the Sequence Listing with their partially decoded sequences.

Example 4

Comparison of Gene Expression Levels by Semi-quantitative PCR

1. Obtaining Samples

Clinical tissue samples of human neuroblastoma (stage 4s) were quasi-aseptically frozen immediately after surgical extraction and then preserved at −80° C. These samples were provided in 8 specimens. In a similar manner, clinical tissue samples of human neuroblastomas of the favorable and unfavorable prognosis types were provided in 12 specimens each.

Prognosis assay of the neuroblastoma samples of the favorable and unfavorable prognosis types was carried out based on the following criteria:

Favorable prognosis type:
Stage 1 or 2
Age of onset: <1
Survival for ≧5 years after surgery without recurrence
No amplification of N-myc
Unfavorable prognosis type:
Stage 4
Age of onset: ≧1
Death within 3 years after surgery
Amplification of N-myc 2. Differential Screening Semi-quantitative RT-PCR of each specimen was performed in the manner described below.

a) Reverse Transcription (RT)

The RNA from the specimen was reverse-transcribed into cDNA using Super Script II reverse transcriptase (GIBCO). Specifically, 48 μl of a solution comprising 20 μg of the total RNA, 8 μl of random primers (1 μg/μl) (Takara Shuzo Co., Ltd.), and sterile ultra-purified water containing DEPC in an amount as necessary was prepared. This solution was incubated at 65° C. for 15 minutes and was placed on ice after the reaction was complete. Sterile ultra-purified water containing 24 μl of 5×first strand buffer (GIBCO), 12 μl of 0.1 M DTT (GIBCO), 30 μl of dNTPs (Takara Shuzo Co., Ltd.), 4 μl of Super Script II reverse transcriptase and 2 μl of DEPC were mixed to prepare 72 μl of a mixed solution. This mixed solution was added to the ice-cooled solution described above to make a total of 120 μl, and was allowed to react at 42° C. for 1.5 hours and then at 95° C. for 5 minutes. This was preserved at −20° C., which was provided for the mother liquor of PCR template.

Thus prepared cDNA solution was diluted with DDW to an appropriate dilution and then it was normalized (concentrations adjusted) with GAPDH primers. The base sequences of the GAPDH primers used were as follows:

```
5'-ACCTGACCTGCCGTCTAGAA-3'
(forward: SEQ ID NO:1077)
and

5'-TCCACCACCCTGTTGCTGTA-3'.
(reverse: SEQ ID NO:1078)
```

Subsequently, each sample with its concentration adjusted by dilution with DDW was subjected to PCR as described below.

b) PCR

PCR was performed with rTaq polymerase (Takara Shuzo Co., Ltd.). Appropriate primers were designed against the genes (whether novel or known) identified in the cDNA library from the stage 4s neuroblastoma. Differential screening of three pairs of cDNA sample populations with their concentrations adjusted was performed. Specifically, 2 μl of cDNA, 5 μl of sterile distilled water, 1 μl of 10×rTaq buffer, 1 μl of 2 mM dNTPs, 0.5 μl each of the synthesized primer set (forward and reverse), and 0.5 μl of rTaq were combined. After denaturing this mixture at 95° C. for 2 minutes, a cycle of 95° C. for 15 seconds, 58° C. for 15 seconds and 72° C. for 20 seconds was repeated 35 times, and then the mixture was allowed to stand at 72° C. for 20 minutes, thereby performing PCR. Where no band showed up, PCR conditions were studied by increasing the number of cycles. Thus, annealing temperatures and cycle numbers for the respective primers could be determined.

The PCR products under thus determined conditions were electrophoresed on 1.5% agarose gel for 20 minutes, stained with ethidium bromide. The concentrations of the bands were compared among three pairs of specimens (i.e., stage 4s neuroblastoma, neuroblastomas of the favorable and unfavorable prognosis types).

As previously described, Table 1 summarizes the obtained patterns according to the specimen subsets. Results from the expressed pattern analysis are as previously discussed.

The primers used were selected under suitable primer selection conditions (base number, Tm, GC %) by inputting into a Primer3 software, the end sequences of the genes to be detected (Example 3). The primer sequences corresponding to the specific clones previously described are provided in the Sequence Listing (SEQ ID NO:175 to SEQ ID NO:1076).

INDUSTRIAL APPLICABILITY

As described above, by utilizing the information obtainable from the genes or the nucleic acids of this invention, the genes are detected in a clinical tissue sample to be assayed thereby to allow the diagnosis for prognosis of neuroblastoma (principally for determining stage 4s neuroblastoma). Specifically, the information obtainable form the genes or the nucleic acids is utilized as tumor markers to allow the preparation of diagnostic agents as well as the design of diagnostic microarrays, both of which can be used for the diagnosis of prognosis.

If the accurate diagnosis of stage 4s neuroblastoma can be made, it will be important information in deciding whether or not the patient in question needs treatment. Where the case warrants, an unnecessary surgical operation may be avoided.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07429451B2). An electronic copy of the "Sequence Listing" will also be available from the USPTO upon request and payment of the fee set forth in 37 CFR 1.19(b)(3).

The invention claimed is:

1. An isolated nucleic acid comprising the nucleic acid sequence set forth in SEQ ID NO:1 in the Sequence Listing.

2. An isolated nucleic acid comprising the full complement to the nucleic acid according to claim 1.

3. An isolated nucleic acid probe comprising:
an isolated nucleic acid selected from the group consisting of the nucleic acid sequence set forth in SEQ ID NO:1 in the Sequence Listing and the full complement of SEQ ID NO:1.

4. A primer containing
an isolated nucleic acid comprising one sequence selected from the group consisting of the nucleic acid sequence set forth in SEQ ID NO:175 and SEQ ID NO:176 in the Sequence Listing, the full complement of SEQ ID NO:175, and the full complement of SEQ ID NO:176.

5. A method for determining whether a subject with neuroblastoma has stage 4s neuroblastoma, the method comprising detecting the presence or absence of the nucleic acid set forth in SEQ ID NO:1 in the Sequence Listing from a clinical tissue sample of neuroblastoma, wherein the presence of SEQ ID NO:1 indicates that the subject has stage 4s neuroblastoma.

6. A nucleic acid microarray comprising a solid phase support and an isolated nucleic acid comprising the nucleic acid sequence set forth in SEQ ID NO:1 in the Sequence Listing immobilized on the solid phase support.

7. A nucleic acid microarray comprising a solid phase support and at least one isolated nucleic acid selected from the group consisting of a the nucleic acid sequence set forth in SEQ ID NO:175 and the nucleic acid sequence set forth in SEQ ID NO:176, wherein the at least one isolated nucleic acid is immobilized on the solid phase support.

8. A method for determining whether a subject with neuroblastoma has stage 4s neuroblastoma, the method comprising detecting the presence or absence of the nucleic acid set forth in SEQ ID NO:1 in the Sequence Listing from a clinical tissue sample of neuroblastoma, wherein the presence of SEQ ID NO:1 indicates that the subject has stage 4s neuroblastoma, and wherein the presence of the nucleic acid sequence set forth in SEQ ID NO:1 is detected by a diagnostic agent comprising the isolated nucleic acid probe according to claim 3.

9. A method for determining whether a subject with neuroblastoma has stage 4s neuroblastoma, the method comprising detecting the presence or absence of the nucleic acid set forth in SEQ ID NO:1 in the Sequence Listing from a clinical tissue sample of neuroblastoma, wherein the presence of SEQ ID NO:1 indicates that the subject has stage 4s neuroblastoma, and wherein the presence of the nucleic acid sequence set forth in SEQ ID NO:1 is detected by a diagnostic kit comprising one pair of the primers according to claim 4.

* * * * *